United States Patent [19]

Narboni

[11] Patent Number: 5,107,861
[45] Date of Patent: Apr. 28, 1992

[54] SAFE EAR CLEAN BUTTON AND PROTECTION WITH ATTACHMENT DEVICE

[76] Inventor: Lillian Narboni, 297 Kingston Ave., #36, Brooklyn, N.Y. 11213

[21] Appl. No.: 625,162

[22] Filed: Dec. 10, 1990

[51] Int. Cl.$^5$ .............................................. A61F 11/00
[52] U.S. Cl. ..................................... 128/864; 128/846
[58] Field of Search ................................ 128/864–868, 128/846; 220/91; 2/2

[56] References Cited

U.S. PATENT DOCUMENTS

| | | | |
|---|---|---|---|
| 3,440,314 | 4/1969 | Frisch | 128/864 X |
| 3,565,069 | 2/1969 | Miller | 128/867 |
| 3,783,864 | 1/1974 | Moller | 128/864 |
| 4,053,051 | 11/1977 | Brinkhoff | 128/867 X |
| 4,055,233 | 10/1977 | Huntress | 128/864 X |

*Primary Examiner*—Robert A. Hafer
*Assistant Examiner*—Brian E. Hanlon
*Attorney, Agent, or Firm*—Goodman & Teitelbaum

[57] ABSTRACT

An ear clean button for cleaning and absorbing the wax and the moisture in a person's ear including a narrow insertion portion for inserting into the person's ear and an enlarged portion to limit the insertion of the insertion portion into the person's ear. An opening extends centrally through the button, and a wax collector is disposed within the opening adjacent to an end surface of the insertion portion for collecting the removed wax. The wax collector includes a hollow cone, a mouth of the cone being disposed at the end surface of the insertion portion with peripheral side walls of the mouth engaging the side walls of the opening, where the closed end of the cone is disposed within the opening. A handle-like introducer is provided for supporting the button, where an end portion of the introducer is removably inserted into the opening of the button from the end surface of the enlarged portion of the button. The end portion of the introducer is provided with an end opening therethrough to receive the cone therein. The introducer has a reduced portion so that the end portion of the introducer can be bent. Preferably, the button is fabricated from a sponge material, and the introducer is fabricated from a plastic material.

11 Claims, 1 Drawing Sheet

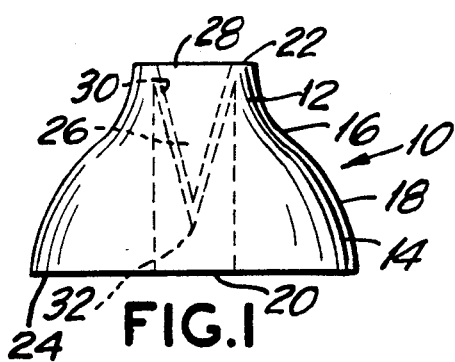
FIG.1
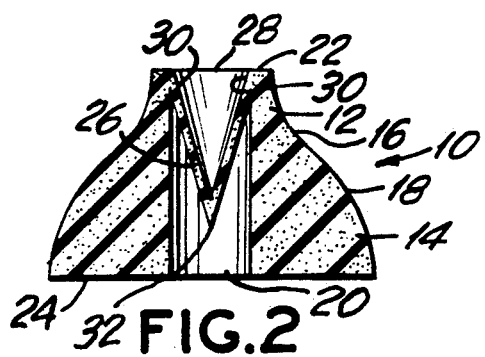
FIG.2
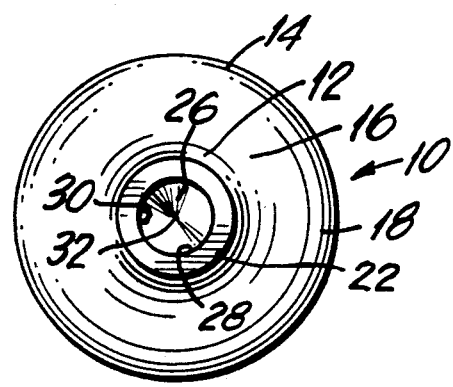
FIG.3
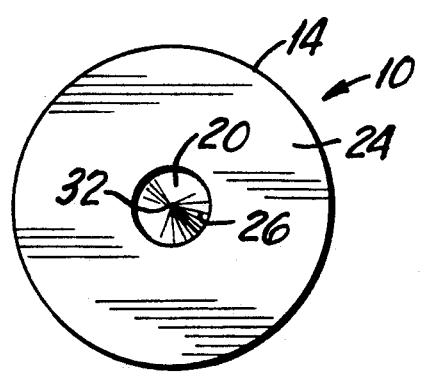
FIG.4
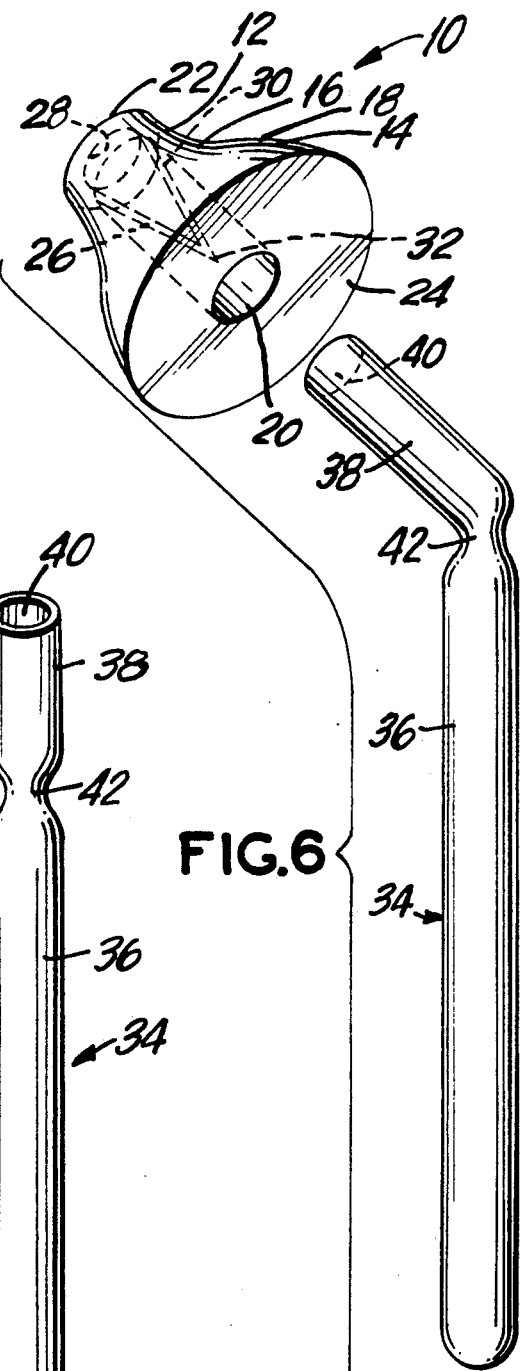
FIG.5
FIG.6

SAFE EAR CLEAN BUTTON AND PROTECTION WITH ATTACHMENT DEVICE

BACKGROUND OF THE INVENTION

1. Field of the Invention

The outer ear serves to gather sound waves. In addition there is also a tube or canal called the meatus that carries the sound waves to the ear drum. The canal which is about an inch and one eighth long, must be kept clean of wax to insure that the sound reaches the drum.

2. Description of the Prior Art

Most people have common problems in cleaning their ears, specially cleaning the ears for others, for instance, children. The danger of inserting the cotton swab too deep into the ear canal, can be quiet serious, where people can hurt themselves and cause damage to their hearing. In any cotton swabs box there's a clear caution reminder: DO NOT ENTER EAR CANAL.

Another serious problem caused many times by cleaning with cotton swabs is hearing loss and infection as a result of the wax compressed towards the ear drum. This invention eliminates those problems.

SUMMARY OF THE INVENTION

The invention is the first step in keeping ears free of wax. It comprises a disposable ear clean button and the introducer. The disposable ear clean button cleans and absorbs the ear wax and moisture during cleaning, preventing the build up of wax around the ear drum through the wax collector, positioned at the inner surface of the ear clean button. The introducer supports the disposable ear clean button during its use. The introducer is especially designed to provide a safe and easy use even children can use, it confidently.

BRIEF DESCRIPTION OF THE DRAWINGS VIEW

FIG. 1 is an elevation view showing the side view of the disposable ear clean button.

FIG. 2 is a sectional view of the FIG. 1 showing the inner surface of the disposable ear clean button.

FIG. 3 is the top view of the FIG. 1.

FIG. 4 is the bottom view of the FIG. 1.

FIG. 5 is a front view of the introducer, the ear clean button supporter.

FIG. 6 is a side view isometric of the introducer and the disposable ear clean button, showing the assembly device.

DESCRIPTION OF THE PREFERRED EMBODIMENT

Referring now to the drawings, FIGS. 1, 2, 3 and 4 show a disposable ear clean button 10 according to the present invention. The disposable ear clean button 10 may be made of any suitable material, such as a sponge material, for the cleaning and absorbing of the wax and the moisture in a person's ear. The button 10 includes a narrow insertion portion 12 for inserting into the person's ear, and an enlarged portion 14 to limit the amount of insertion into the person's ear. The sides 16 of the insertion portion 12 are concave, and the sides 18 of the enlarged portion 14 are convex, where the concave sides 16 and the convex sides 18 form a continuous surface. An opening 20 is provided centrally through the button 10 extending the complete length of the button 10 from one end surface 22 of the insertion portion 12 to the opposite end surface 24 of the enlarged portion 14.

A wax collector 26 is provided within the opening 20, the wax collector 26 being a hollow cone. The mouth 28 of the cone-shaped wax collector 26 is disposed at the end surface 22 of the insertion portion 12 with the peripheral side walls 30 of the mouth 28 engaging the side walls of the opening 20. Preferably, the wax collector 26 forms an integral part of the button 10, where the peripheral side walls 30 of the mouth 28 are connected, in a one piece construction, to the side walls of the opening 20 at the end surface 22. The length of the wax collector 26 is less than the length of the opening 20 which extends through the button 10 so that the closed end 32 of the cone-shaped wax collector 26 is disposed within the opening 20. Accordingly, the wax collector 26 provides means for collecting the removed wax from the person's ear during the use of the button 10, thus preventing any compression of the wax into the ear channel towards the ear drum.

FIGS. 5 and 6 show an introducer 34 which acts as handle means to support the button 10. The introducer 34 is an elongated tube member 36 having a short hollow end portion 38 provided with an end opening 40 therethrough. A reduced portion 42 is provided adjacent to the end portion 38 so that the end portion 38 can be bent, as shown in FIG. 6. Preferably, the length of the end portion 38 is approximately equal to the length of the opening 20 in the button 10. The introducer 34 is preferably fabricated from a firm and durable material, such as plastic.

In use, the introducer 34 is attached to the button 10 by inserting the end portion 38 into the opening 20 at the end surface 34 of the enlarged portion 14 so that the wax collector 36 is received in the end opening 40 of the end portion 38. The end portion 38 is pushed into the opening 20 until the free end of the end portion 38 engages the peripheral side walls 30 of the mouth 28 of the cone-shaped wax collector 26 at the end surface 22 of the insertion portion 12 so that a secure attachment is made therebetween. The person now holds the introducer 34 in his hand and inserts the insertion portion 12 of the button 10 into his ear for a safe cleaning thereof, where the enlarged portion 14 prevents any deep insertion of the button 10 into the person's ear, thus providing a safe means for cleaning and protecting the person's ears without the risk of dangerous side effects. The present invention may be used by children and persons from the age of seven years and up, where the button 10 may also be manufactured in a special smaller size for infants and children up to the age of seven years.

Though the embodiment of the invention described above functions as means for keeping a person's ears free of wax so that the wax does not compress towards the ear drum during the use thereof, the button 10 may have multiple other features. The button 10 can be a real relief for people who often swim and are frequently affected by hearing losses, since wearing one button 10 in each ear, without the introducer 34, protects the person's ears without compressing the wax towards the ear drum. After swimming, the buttons 10 are removed, where the wax collectors 26 will retain any wax that was in the person's ears. In other words, the person's ears are cleaned while the person swims. Furthermore, the buttons 10 when worn by a person going to sleep, can be the answer to provide sound sleep. Additionally, the buttons 10 can be worn by a person to avoid noise created at crowded places, or can be worn just to provide some peaceful and quiet moments that are sometimes necessary during long flights, etc.

It is noted, that the combination of the spherical shape and the flexibility of the button 10 is very compatible to any ear shape.

I claim:

1. An ear clean button comprising:
    a narrow insertion portion for inserting into a person's ear;
    an enlarged portion connected to said insertion portion to limit insertion of said insertion portion into the person's ear;
    an opening extending centrally through said button from one end surface of said insertion portion to an opposite end surface of said enlarged portion; and
    wax collector means disposed within said opening adjacent to said one end surface of said insertion portion for collecting removed wax from the person's ear during use of said button;
    said wax collector means including a hollow cone, a mouth of said cone being disposed at said one end surface of said insertion portion with peripheral side walls of said mouth engaging said walls of said opening, the diameter of said cone at said mouth being equal to a diameter of said opening.

2. An ear clean button according to claim 1, wherein said cone has a length less than length of said opening so that a closed end of said cone is disposed within said opening.

3. An ear clean button according to claim 1, wherein said cone is an integral part of sad button so that said peripheral side walls of said mouth are connected to said side walls of said opening at said one end surface of said insertion portion in a one piece construction.

4. An ear clean button according to claim 1, wherein sides of said insertion portion are concave and sides of said enlarged portion are convex to provide a continuous outer surface on sides of said button.

5. An ear clean button according to claim 1, wherein said button is fabricated from a sponge material.

6. An ear clean button according to claim 1, wherein said cone has a length less than length of said opening so that a closed end of said cone is disposed with said opening, said cone being an integral part of said button so that said peripheral side walls of said mouth are connected to said side walls of said opening at said one end surface of said insertion portion in a one piece construction, sides of said insertion portion being concave and sides of said enlarged portion being convex to provide a continuous outer surface on sides of said button, and said button being fabricated from a sponge material.

7. An ear clean button according to claim 6, wherein said button is provided with handle means for supporting said button, said handle means including an introducer having an end portion removably inserted into said opening of said button from said opposite end surface of said enlarged portion, said introducer being an elongated tube member, said end portion of said introducer being hollow and being provided with an end opening therethrough to receive said cone therein, said introducer having a reduced portion adjacent to said end portion thereof so that said end portion of said introducer can be bent, and said introducer being fabricated from a plastic material.

8. An ear clean button according to claim 1, wherein said button is provided with handle means for supporting said button, said handle means including an introducer having an end portion removably inserted into said opening of said button from said opposite end surface of said enlarged portion.

9. An ear clean button according to claim 8, wherein said introducer is an elongated tube member, and said end portion of said introducer is hollow and is provided with an end opening therethrough to receive said cone therein.

10. An ear clean button according to claim 8, wherein said introducer has a reduced portion adjacent to said end portion thereof so that said end portion of said introducer can be bent.

11. An ear clean button according to claim 8, wherein said introducer is fabricated from a plastic material.

* * * * *